United States Patent [19]

Samaras et al.

[11] Patent Number: 4,858,616

[45] Date of Patent: Aug. 22, 1989

[54] BLOOD PRESSURE MEASUREMENT SYSTEM FOR FILTERING LOW-FREQUENCY, HIGH-AMPLITUDE NOISE

[75] Inventors: George M. Samaras, Columbia, Md.; Steven M. Falk, Washington, D.C.

[73] Assignee: GMS Engineering Corporation, Columbia, Md.

[21] Appl. No.: 169,587

[22] Filed: Mar. 17, 1988

[51] Int. Cl.$^4$ .............................................. A61B 5/02
[52] U.S. Cl. ..................................... 128/680; 128/679
[58] Field of Search ............... 128/672, 677, 678, 679, 128/680, 682, 683, 681

[56] References Cited

U.S. PATENT DOCUMENTS

| | | | |
|---|---|---|---|
| 3,348,534 | 10/1967 | Marx et al. | 128/679 |
| 3,581,734 | 6/1971 | Croslin et al. | 73/725 |
| 4,144,879 | 3/1979 | Nakayama et al. | 128/680 |
| 4,649,928 | 3/1987 | Samaras et al. | 128/670 |

FOREIGN PATENT DOCUMENTS 0154995  9/1985  European Pat. Off. ............ 128/682

Primary Examiner—Ruth S. Smith
Assistant Examiner—K. Schaetzle
Attorney, Agent, or Firm—Indyk, Pojunas & Brady

[57] ABSTRACT

A noise-immune blood pressure measurement system filters out high frequency noise and blood pulses. The system also recognizes and filters out slow, large noise signals in the range of 0.5 Hz. Such noise signals result when a patient wearing the system makes slow, large finger movements, or is slowly transported by a vehicle over a large bump, for instance. The system accurately derives systolic, mean arterial, and diastolic pressures even when used in a noisy emergency vehicle or battlefield situation.

12 Claims, 6 Drawing Sheets

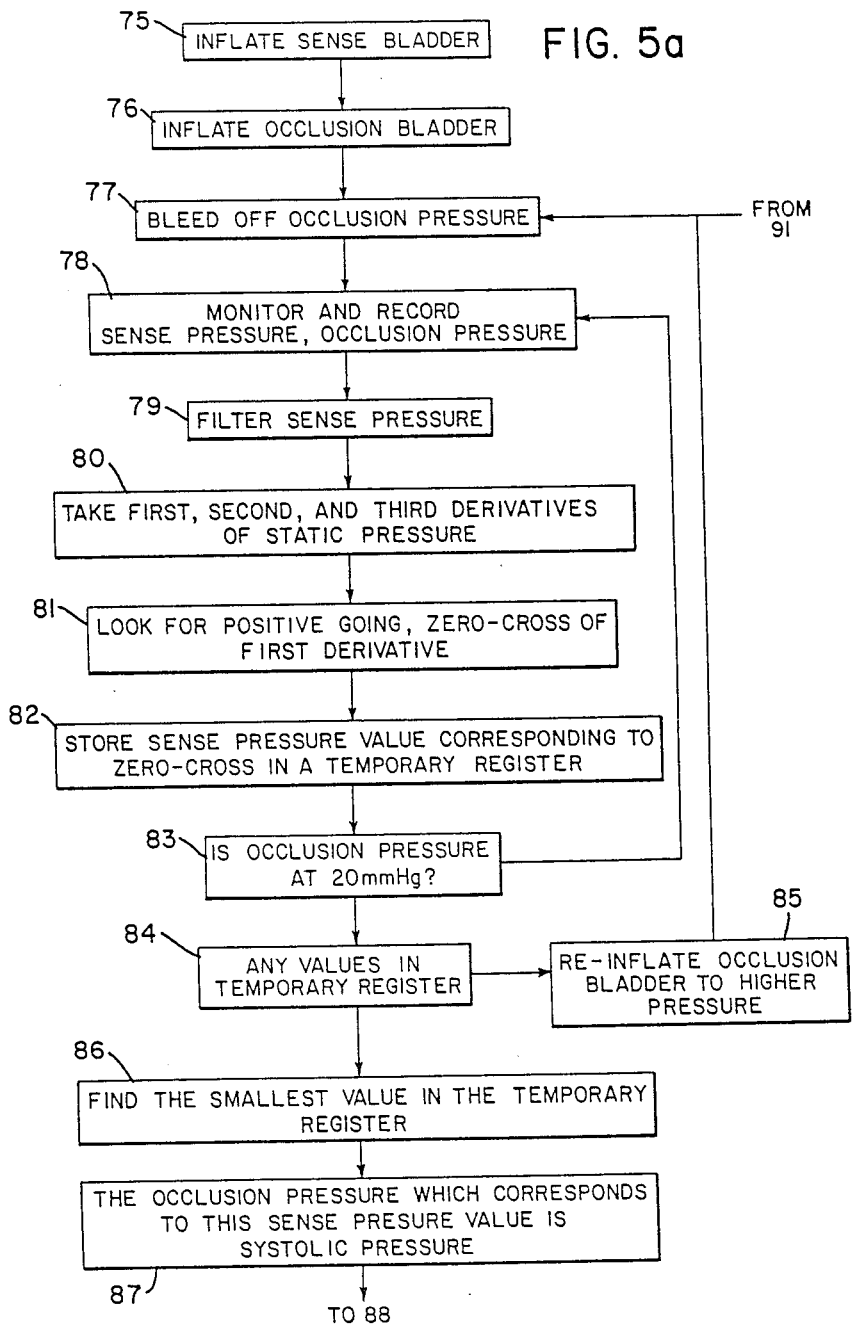

BLOOD PRESSURE MEASUREMENT SYSTEM FOR FILTERING LOW-FREQUENCY, HIGH-AMPLITUDE NOISE

Governmental Interest

The U.S. Government may have rights in this invention under Contract No. DAMD17-86-C-6067 with the U.S. Army Medical and Research Command.

FIELD OF THE INVENTION

This invention concerns a blood pressure measurement system. More particularly, the invention concerns a blood pressure measurement system that filters low-frequency, high-amplitude noise to accurately measure blood pressure.

BACKGROUND OF THE INVENTION

Blood pressure measurement is used to generally indicate the health of a patient or the type of emergency treatment which is necessary for an accident victim or a battlefield casualty. Most blood pressure measurement systems involve listening for blood pulses of a patient with a stethoscope. Noises of an emergency vehicle or in a battlefield make these pulses difficult to hear, which makes accurate measurement of blood pressure very difficult to obtain.

FIG. 1 shows a schematic diagram of a blood pressure measurement system that determines systolic, diastolic, and mean arterial pressures without detecting blood pulses. The blood pressure measurement system of FIG. 1 is particularly useful in emergency vehicles and battlefield situations, where movement and noise drastically affect accurate measurement of blood pressure in systems that rely on the detection of blood pulses. The system of FIG. 1 filters out blood pulses and high frequency noise, and processes signals having frequencies on the order of 1 Hz.

The operation of the blood pressure measurement system of FIG. 1 is detailed in U.S. Pat. No. 4,649,928 to Samaras et al., which has been assigned to the same entity as this invention. This application incorporates the disclosure of U.S. Pat. No. 4,649,928 by reference.

FIG. 1 shows an occlusion bladder 10 on the upper arm 8 of a patient, which is inflated to a pressure substantially higher than systolic blood pressure of the patient to stop blood flow in the upper limb 8. A lower sensing bladder 12 on the forearm 6 of the patient is inflated to a nominal value, such as 70 mmHg. Pressure in the occlusion bladder 10 is gradually decreased over a period of approximately thirty seconds. A microprocessor 28 controls valves 16, 18, and 20 and controls pump 14 to inflate and deflate the occlusion bladder 10 and the sensing bladder 12. Transducers 22 and 24 monitor pressures in the occlusion bladder 10 and the sensing bladder 12, respectively. These transducers 22 and 24 respectively produce an occlusion pressure signal and a sensing pressure signal which are received by a microprocessor 28. The microprocessor 28 filters out pulses corresponding to a patient's heart beat from the sensing pressure signal produced by the transducer 24.

An occlusion pressure value sensed by the transducer 22 on the occlusion bladder 10 corresponds to systolic pressure of a patient when the sensing pressure signal from the sensing bladder 12 reaches a minimum value. The microprocessor 28 derives first, second, and third time derivatives of the sensing pressure signal from the sensing bladder 12. An occlusion pressure value from the occlusion bladder 10 corresponds to mean arterial pressure when the third time derivative of the sensing pressure signal is a positive-going, zero-crossing signal. The microprocessor 28 derives diastolic pressure from the mean arterial pressure and the systolic pressure according to a well known relationship.

The present inventors have found that the system of FIG. 1 is somewhat responsive to very low-frequency, high-amplitude noise signals, which can cause the system of FIG. 1 to produce false values of systolic, mean arterial, and diastolic pressures. These noise signals are produced when a patient wearing the system is slowly transported by an emergency vehicle over a large bump, for instance. These noise signals are also produced when a patient wearing the system makes slow, large movements with his fingers, for instance. In an emergency situation, it is critical to accurately measure these pressures for correct treatment of a patient. Thus, a need exists for determining the presence of such slow, large noise signals and for filtering out these noise signals to accurately 10 measure blood pressure of a patient.

SUMMARY OF THE INVENTION

The invention concerns a blood pressure measurement system comprising an occlusion bladder attachable to a patient's upper limb, a sensing bladder attachable to a patient's lower limb, and a means for monitoring pressures in the occlusion bladder and sensing bladder. The system also comprises a means for filtering out blood pulse signals from the sensing pressure signal to produce a static pressure signal, a means for recognizing and storing a plurality of relative minimums of the static pressure signal, and a means for relating the smallest relative minimum with a corresponding occlusion pressure to derive systolic pressure of the patient.

The blood pressure measurement system of this invention is immune to high frequency noise and does not involve listening for blood pulses of a patient. The system is also immune to slow, large noise signals.

It is an object of this invention to recognize slow, large noise signals to which a blood pressure measurement system responds.

It is another object of this invention to filter out these slow, large noise signals from a blood pressure measurement system for accurate measurement of blood pressures.

BRIEF DESCRIPTION OF THE FIGURES

FIGS. 5a and 5b show a flow chart illustrating steps for determining and filtering slow, large noise signals out of the system of FIG. 1 according to this invention.

DETAILED DESCRIPTION OF FIGURES

Figure 1:
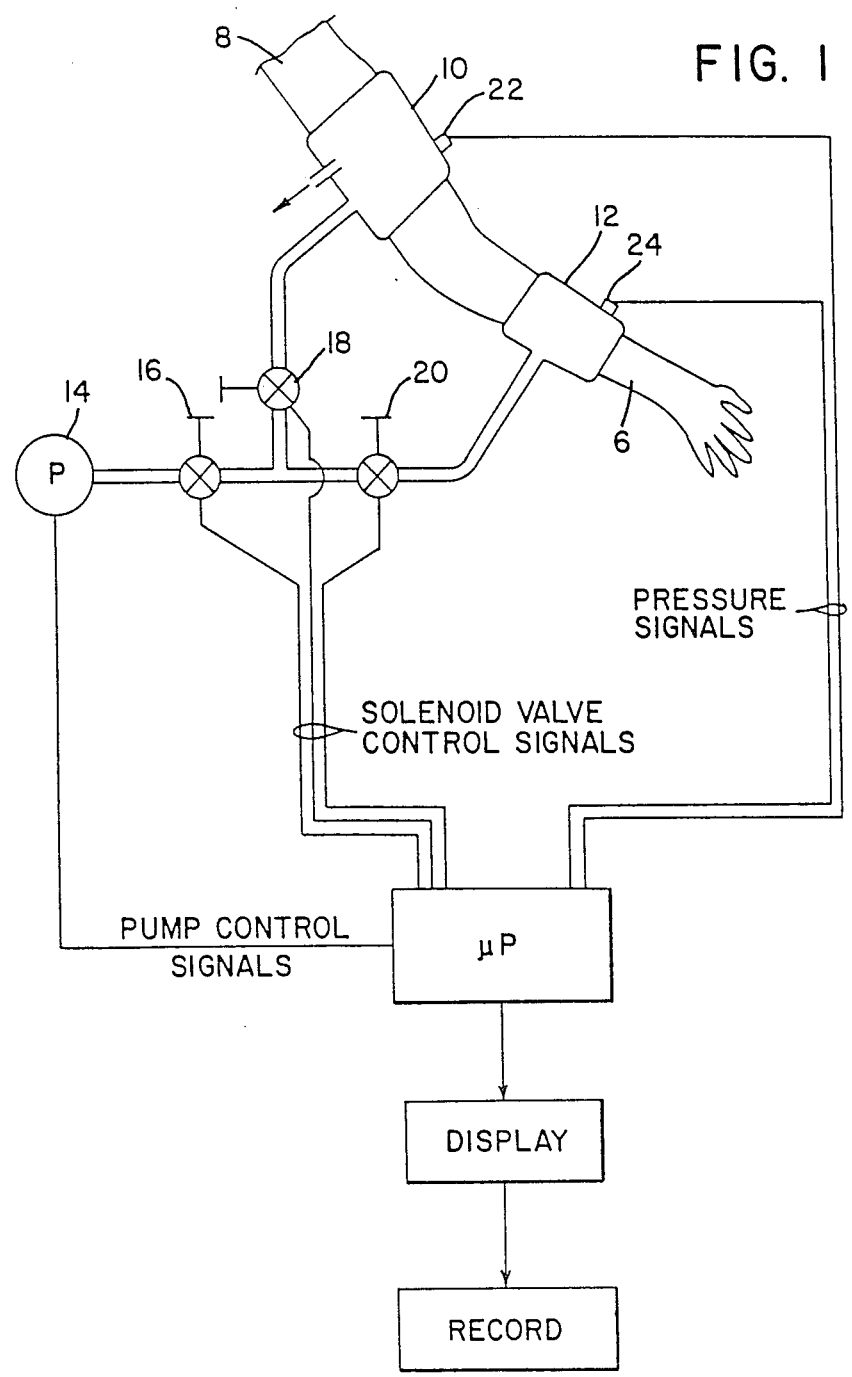
FIG. 1 is a schematic diagram of a blood pressure measurement system, comprising the environment of the present invention.
Figure 2:
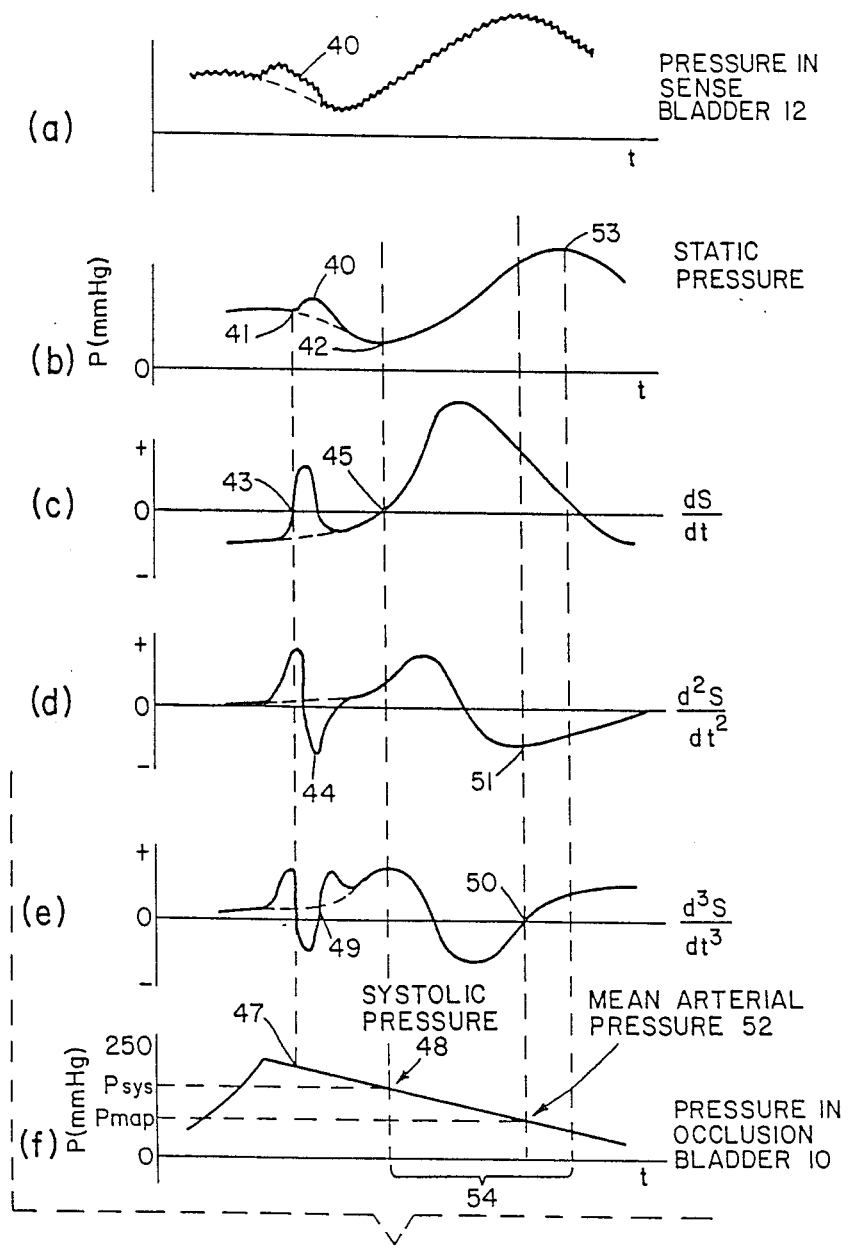
FIGS. 2(a)–(f) illustrate waveforms related to the system of FIG. 1 when responding to slow, large noise signals before sensing systolic pressure, as recognized according to this invention.

The present inventors have identified waveforms related to the system of FIG. 1, when that system is responsive to slow, large noise signals that occur before systolic pressure of a patient is reached. FIGS. 2(a)–(f) illustrate these waveforms. Pressure in mmHg is plotted on the vertical axis and time in seconds is plotted on the horizontal axis in FIGS. 2(a), 2(b), and 2(f). FIGS. 2(c), 2(d), and 2(e) respectively illustrate first, second, and third time derivatives of the curve of FIG. 2(b). Negative and positive values are plotted on the vertical axis and time is plotted on the horizontal axis in FIGS. 2(c), 2(d), and 2(e).

FIG. 2(a) shows a sensing pressure signal produced by the transducer 24 on the sense bladder 12. As an occlusion bladder 10 is slowly deflated, blood fills the limb of a patient and pressure in the limb changes according to the curve of FIG. 2(a). The present inventors have recognized that a rise 40 occurs in the curve when the blood pulse measurement system of FIG. 1 is responsive to a slow, large noise signal that occurs before systolic pressure of a patient has been reached. Such a slow, large noise signal is on the order of 0.5 Hz and results when a patient makes large and slow finger movements, for instance. These noise signals result if a patient continually and gradually clenches his relaxed hand once or spreads the fingers of his relaxed hand once during 10–30% of the time necessary to bleed pressure from the occlusion bladder 10, for example. Somewhat smaller finger movements during this time will also cause the blood pressure measurement system of FIG. 1 to produce a rise 40 in response to slow, large noise signals. Slow, large noise signals also result when a patient wearing the system of FIG. 1 is slowly transported in a vehicle over a bump, for instance. These noise signals result if a patient is transported over a speed-bump at 10–15 mph, for example.

The curve of FIG. 2(a) would follow the dashed portion of the curve and the rise 40 would not be present in the curve, if no slow, large noise signals are present. The transducer 24 senses blood pulses as a limb fills with blood, which causes oscillations in the curve of FIG. 2(a).

FIG. 2(b) shows a static pressure curve. Though pressure changes in the limb of a patient, and the curve of FIG. 2(b) changes accordingly, the curve of FIG. 2(b) is static in that this curve shows no oscillations. This static pressure results after blood pulses are filtered in a manner as described in U.S. Pat. No. 4,649,928 from the sensing pressure signal of FIG. 2(a). FIG. 2(b) shows two relative minimums 41 and 42, which result when the system of FIG. 1 is responsive to a single slow, large noise signal 40. A single noise signal is shown as an example, though numerous slow, large noise signals might occur during measurement of a patient's blood pressure.

FIG. 2(c) shows two positive-going, zero-crosses, 43 and 45, corresponding to the relative minimums 41 and 42 in the static pressure curve of FIG. 2(b). According to the present invention, the positive-going, zero-crosses 43 and 45 are recognized when negative values of the first derivative of FIG. 2(c) change to positive values. For each of these positive-going, zero-crosses 43 and 45, a corresponding value of static pressure and occlusion pressure is determined and stored.

As recognized by the inventors, the value of occlusion pressure corresponding to the smallest value of static pressure equals systolic pressure. FIG. 2(f) represents an occlusion pressure signal from the transducer 22 on the occlusion cuff 10. FIG. 2(f) shows an occlusion pressure value 47 corresponding in time to the zero-cross 43 of the first derivative of FIG. 2(c) and an occlusion pressure value 48 corresponding to the zero-cross 45 of the first derivative of FIG. 2(c). The static pressure value 42 is smaller than the value 41. The occlusion pressure value 48 corresponds to the smaller static pressure value 42 and equals systolic pressure.

Systolic blood pressure is the highest level of blood pressure occurring in a patient and is measured first, as pressure in the occlusion bladder 10 is decreased. After systolic pressure has been determined, a region 54 of the static pressure curve of FIG. 2(b) is defined to determine mean arterial pressure. This region 54 of the static pressure curve begins when systolic pressure occurs at 42 and ends with a maximum value 53 occurring in the static pressure curve after systolic pressure 42 has occurred.

The third derivative of FIG. 2(e) illustrates two positive-going, zero-crosses 49 and 50. The zero-cross 49 is caused by the slow, large noise signal. Zero-cross 49 is a false indication of mean arterial pressure and is identified as such because the zero-cross 49 occurs before systolic pressure 48. The zero-cross 50 occurs within region 54. The present inventors have recognized that the occlusion pressure value 52 corresponding to the zero-cross 50 equals mean arterial pressure.

Diastolic pressure is derived based on the values for systolic pressure and mean arterial pressure according to a known relationship: diastolic equals ½(3·mean arterial 10 pressure-systolic pressure).

Figure 3:
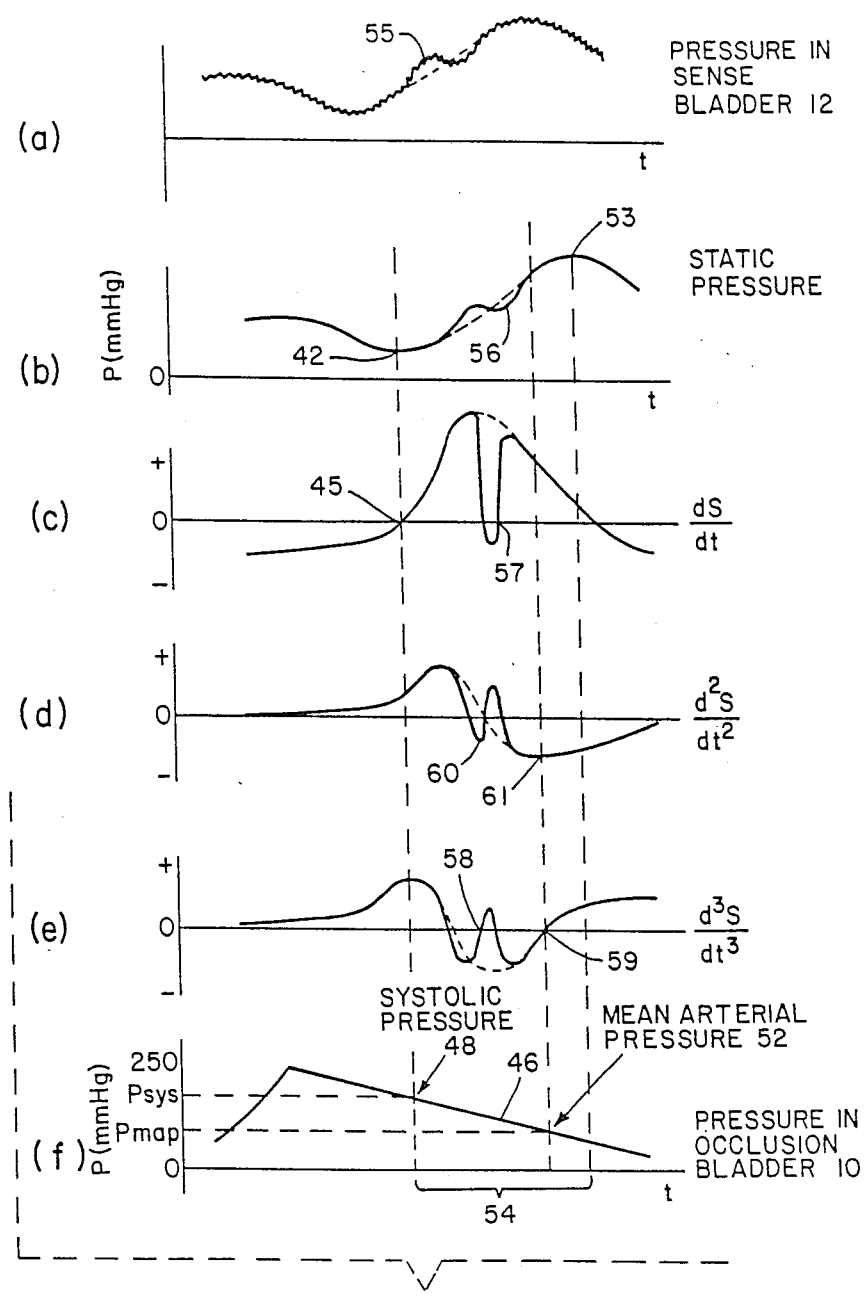
FIGS. 3(a)–(f) illustrate waveforms related to the system of FIG. 1 when responding to slow, large noise signals after sensing systolic pressure and before sensing mean arterial pressure, as recognized according to this invention.

The present inventors have identified waveforms related to the system of FIG. 1 when that system is responsive to slow, large noise signals that occur after systolic pressure of a patient is reached. FIGS 3(a)–(f) illustrate these waveforms. Pressure in mmHg is plotted on the vertical axis and time is plotted in seconds on the horizontal axis in FIGS. 3(a), 3(b), and 3(c). FIGS. 3(c), 3(d), and 3(e) respectively illustrate first, second, and third time derivatives of the curve of FIG. 3(b). Negative and positive values are plotted on the vertical axis and time is plotted on the horizontal axis in FIGS. 3(c), 3(d), and 3(e).

FIG. 3(a) shows a pressure sensing signal produced by the transducer 24 on the sensing bladder 12. The present inventors have recognized that a rise 55 occurs in the curve when the system of FIG. 1 is responsive to a slow, large noise signal that occurs after systolic pressure of a patient has been reached and before mean arterial pressure has been reached. The curve of FIG. 3(a) would follow the dashed portion of the curve and the rise 55 would not be present in the curve, if no slow, large noise signals are present. The transducer 24 senses blood pulses as a limb fills with blood, which causes oscillations in the curve of FIG. 3(a).

FIG. 3(b) illustrates a static pressure curve after filtering of blood pulses in a manner as described in U.S. Pat. No. 4,649,928. The static pressure curve of FIG. 3(b) two relative minimums 42 and 56, which result when the system of FIG. 1 is responsive to a single slow, large noise signal 55.

FIG. 3(c) shows two positive-going, zero-crosses 45 and 57 corresponding to the relative minimums 42 and 56 of the static pressure curve of FIG. 3(b). According to the present invention, the positive-going, zero-crosses 45 and 57 are recognized when negative values of the first derivative of FIG. 3(c) change to positive values. For each of these positive-going, zero-crosses 45 and 57, a corresponding value of static pressure is determined and stored. The relative minimums 42 and 56 of FIG. 3(b) respectively correspond to the zero-crosses 45 and 57 of FIG. 3(c).

As recognized by the inventors, the value of occlusion pressure corresponding to the smallest value of static pressure equals systolic pressure. FIG. 3(f) represents an occlusion pressure signal from the transducer 22 on the occlusion cuff 10. FIG. 3(f) shows an occlusion pressure value 48 corresponding in time to the zero-cross 45 of the first derivative of FIG. 3(c) and an occlusion pressure value 46 corresponding to the zero-cross 57 of the first derivative of FIG. 3(c). In this case, the static pressure value 42 is less than the value 56. The occlusion pressure value 48 corresponds to the smaller static pressure value 42 and equals systolic pressure.

After systolic pressure has been determined, a region 54 of the static pressure curve of FIG. 3(b) is defined to determine mean arterial pressure. This region 54 of the static pressure curve begins when systolic pressure occurs at 42 and ends with a maximum value 53 occurring in the static pressure curve after systolic pressure 42 has occurred.

The third derivative of FIG. 3(e) shows two positive-going, zero-crosses 58 and 59. The zero-cross 58 is caused by the slow, large noise signal. Both zero-crosses 58 and 59 occur within region 54.

According to the invention, negative values 60 and 61 of the second derivative of FIG. 3(d) are stored in a temporary register, which correspond to positive-going, zero-crossings 58 and 59 of the third derivative of FIG. 3(e). The present inventors have discovered that the most negative value of the second derivative stored in the temporary register, corresponds to an occlusion pressure value that equals mean arterial pressure. In this example, the more negative value of the second derivative is at 61. The occlusion pressure value 52, corresponding to the more negative value 61 of the second derivative, equals mean arterial pressure. Diastolic pressure is derived based on the values for systolic pressure and mean arterial pressure.

Figure 4:
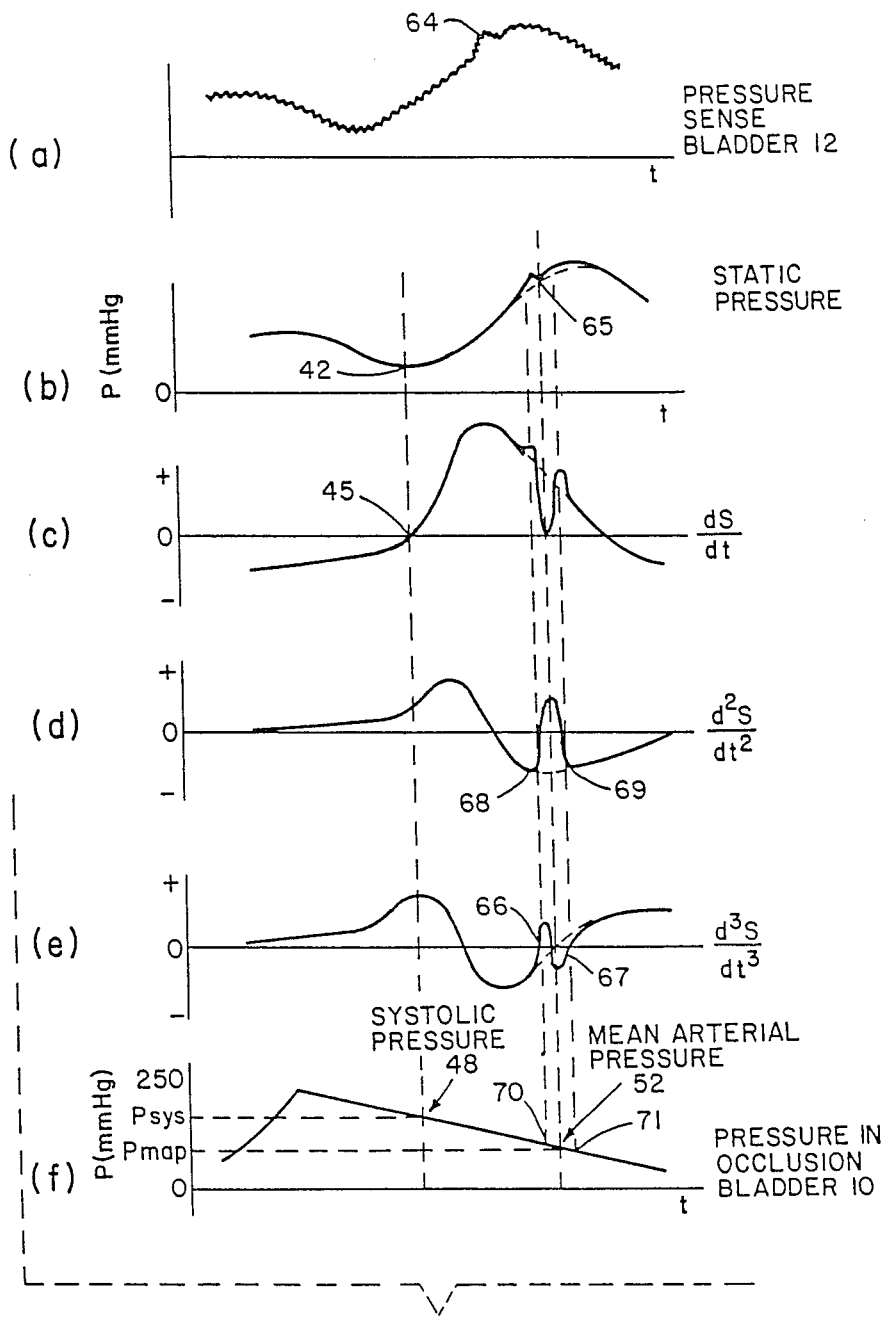
FIGS. 4(a)–(f) illustrate waveforms related to the system of FIG. 1 when responding to slow, large noise signals when sensing mean arterial pressure, as recognized according to this invention.

The present inventors have identified waveforms related to the system of FIG. 1 when that system is responsive to slow, large noise signals at the same time mean arterial pressure of a patient is reached. FIGS 4(a)-(f) illustrate these waveforms. Pressure in mmHg is plotted on the vertical axis and time in seconds is plotted on the horizontal axis in FIGS. 4(a), 4(b), and 4(f). FIGS. 4(c), 4(d), and 4(e) respectively illustrate first, second, and third time derivatives of the curve of FIG. 4(b). Negative and positive values are plotted on the vertical axis and time is plotted on the horizontal axis in FIGS. 4(c), 4(d), and 4(e).

FIG. 4(a) shows the sensing pressure signal from the transducer 24 of the sense bladder 12. A rise 64 occurs in the curve in response to a single slow, large noise signal. FIG. 4(b) shows a waveform illustrating static pressure sensed by the transducer 24 on the sensing bladder 12 after blood pulses have been filtered in a manner as described in U.S. Pat. No. 4,649,928 from the curve of FIG. 4(a). The static pressure signal of FIG. 4(b) has two relative minimums, 42 and 65, which result when the system of FIG. 1 is responsive to a single, slow, large noise signal 64 occurs at the same time mean arterial pressure is reached. FIG. 4(c) illustrates one positive-going, zero-cross 45 corresponding to a minimum static pressure value 42 and an occlusion pressure value 48. The occlusion pressure value 48 equals systolic pressure, as discussed concerning FIGS. 2(b), 2(c), and 2(f), for instance.

FIG. 4(e) shows the third derivative of the static pressure curve of FIG. 4(b). FIG. 4(e) illustrates two positive-going, zero-crosses 66 and 67 which result when the slow, large noise signal 64 occurs. Negative values 68 and 69 of the second derivative of 4(d) respectively correspond to these positive-going, zero-crosses 66 and 67. These negative values 68 and 69 of the second derivative of FIG. 2(d) can be equal when the slow, large noise signal 64 occurs at the same time mean arterial pressure is reached. In this situation, two values of occlusion pressure 70 and 71, corresponding to the two equal negative values 68 and 69 of the second derivative, are averaged to yield an occlusion pressure value 52. According to this invention, occlusion pressure value 52 equals mean arterial pressure. Diastolic pressure is derived based on the values for systolic pressure and mean arterial pressure as discussed above.

FIG. 5(a) shows a flow chart illustrating steps performed by circuitry in the microprocessor 28 of FIG. 1 according to this invention. The microprocessor 28 regulates the pump 14 and valve 16, 18, and 20 to inflate the sense bladder 12 and occlusion bladder 10 at steps 75 and 76, respectively. At step 77, pressure in the occlusion bladder 10 is bled off slowly at 6 mmHg per second, for instance. As pressure in the occlusion bladder 10 reduces, blood begins to fill the limb of the patient. At step 78, the microprocessor 28 monitors the output of the transducer 22 and transducer 24 and records the resulting sensing pressure signal and the occlusion pressure signal. At step 79, the microprocessor 28 filters blood pulses from the output of the sensing pressure signal in a manner as described in U.S. Pat. No. 4,649,928 to produce a static pressure signal corresponding to FIG. 2(b), for instance. At step 80, the microprocessor 28 takes first, second, and third derivatives of the static pressure curve. At step 81, the microprocessor 28 searches for positive-going, zero-crosses in the first derivative of the static pressure curve, such as 43 and 45 in FIG. 2(b), for example.

At step 82, the microprocessor 28 stores in a temporary register a static pressure value for each corresponding zero-cross of the first derivative. FIG. 2(c) shows two positive-going, zero crosses 43 and 45. Thus, the microprocessor 28 stores corresponding static pressure values 41 and 42 of the curve of FIG. 2(b). At step 83, the microprocessor 28 determines if pressure in the occlusion bladder 10 has dropped to 20 mmHg, for instance. If the pressure in the occlusion bladder 10 has not yet dropped to 20 mmHg, the monitoring and recording of pressures in the occlusion bladder 10 and sense bladder 12 continues, from step 78 and pressure in the occlusion bladder 10 continues to decrease. If the pressure in the occlusion bladder 10 has dropped to 20 mmHg, the microprocessor 28 has accumulated enough information to derive systolic, mean arterial and diastolic pressures.

At step 84, the microprocessor 28 determines if any values representing static pressure values, such as 41 or 42, in FIG. 2(b) have been stored in the temporary register. If no values have been stored in the register, the initial pressure of the occlusion bladder 10 might have been lower than the systolic pressure of the patient. Thus, at step 85, the microprocessor 28 controls the pump 14, valves 16, 18, and 20 to reinflate the occlusion bladder 10 to a pressure which is higher than 70 mmHg above a typical systolic pressure and steps 77–84 repeat. If static pressure values have been stored in the register, the microprocessor 28 finds the smallest of these values at step 86.

At step 87, the microprocessor 28 relates this smallest static pressure value to an occlusion pressure value to derive systolic pressure. FIG. 2(b) shows the smallest stored instantaneous value of static pressure value at 42. FIG. 2(f) shows the corresponding occlusion pressure at 48. The occlusion pressure value 48 is equal to systolic pressure.

Figure 5B:
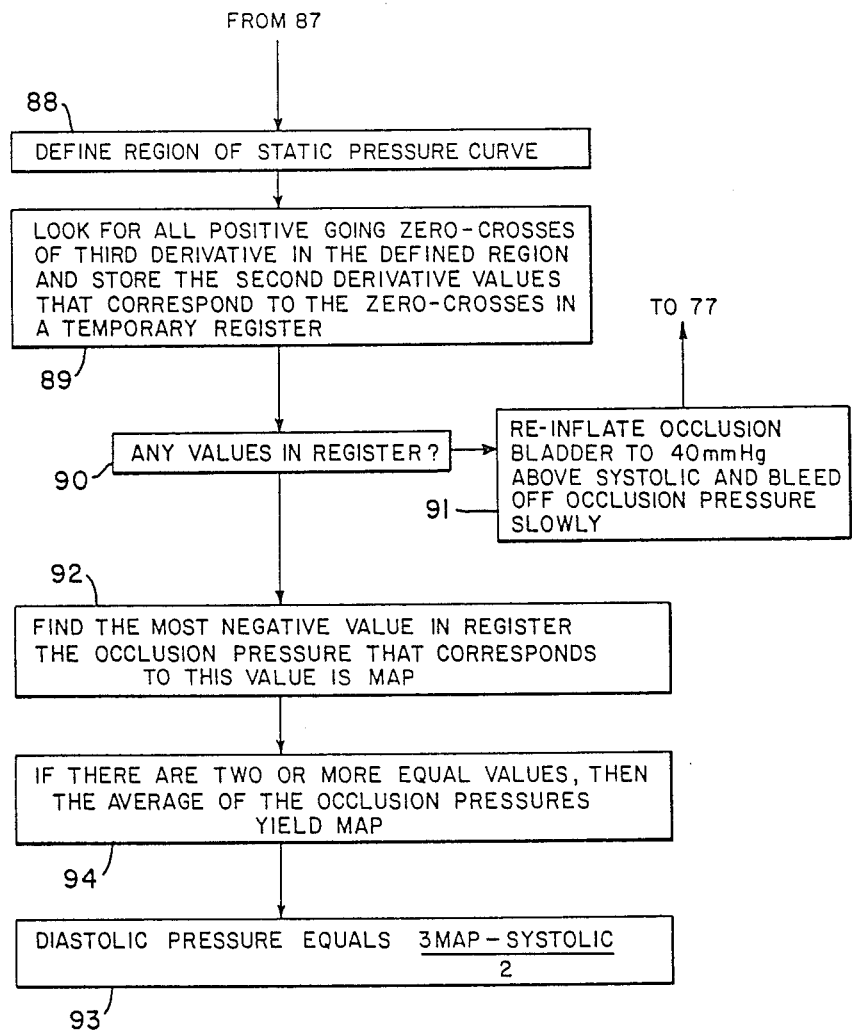

FIG. 5(b) shows a continuation of a flow chart of FIG. 5(a) and illustrate more steps performed by circuitry in the microprocessor 28 according to this invention. At step 88, a microprocessor 28 defines a region 54 of the static pressure curve of FIG. 2(b). Mean arterial pressure is found within this region 54. The region 54 begins with systolic pressure 42 of the static pressure curve of FIG. 2(b) and extends to a maximum point 53 of the static pressure curve.

At step 89, the microprocessor 28 examines the third derivative of FIG. 2(e) for positive-going, zero-crosses, for instance. The microprocessor 28 then stores negative values of the second derivative of FIG. 2(d), which correspond to these zero-crosses, in another temporary register. For example, the third derivative of FIG. 2(e) shows two positive-going, zero-crosses 49 and 50. A value 44 of the second derivative of FIG. 2(d), corresponding to the zero-cross 49, is not stored in the register, because the zero-cross 49 does not fall within the defined region 54. A value 51 of the second derivative of FIG. 2(d) corresponding to the zero-cross 50 is stored in the temporary register, because the zero-cross 50 of the third derivative of FIG. 2(e) falls within the defined region 54.

At step 90, the microprocessor 28 examines the temporary register to see if any negative values of the second derivative are present. If not, at step 91, the microprocessor reinflates the occlusion bladder to 40 mmHg above the systolic pressure which has been determined at step 87. The occlusion bladder pressure is reduced at a slower rate equaling 4 mmHg per second, approximately, and the steps 77–89 of FIGS. 5(a) and 5(b) repeat. If values are present in the temporary register according to step 90, the most negative value of the second derivative in the temporary register is found by the microprocessor 28 at step 92. An occlusion pressure value that corresponds to this most negative value of the second derivative in the register is equal to mean arterial pressure. For instance, FIG. 2(d) shows the most negative value of the second derivative at 51. The corresponding occlusion pressure value is 52 in FIG. 2(f), which is the mean arterial pressure of the patient.

Steps 75–80 of FIG. 5(a) are the same as described above when filtering out slow, large noise signals that occur after systolic pressure and before mean arterial pressure.

At step 81, the microprocessor 28 searches for positive-going, zero-crosses in the first derivative of FIG. 3(c). At step 82, the microprocessor 28 stores in a temporary register a static pressure value for each corresponding zero-cross of the first derivative. FIG. 3(c) shows two positive-going, zero-crosses 45 and 57. Thus, the microprocessor 28 stores corresponding static pressure values 42 and 56 of FIG. 3(b). At step 83, the microprocessor 28 determines if the pressure in the occlusion bladder 10 has dropped to 20 mmHg, and the microprocessor 28 has accumulated enough information to derive systolic, mean arterial and diastolic pressures, as described above.

At step 84, the microprocessor 28 determines if any static pressure values, such as 42 or 56 in FIG. 3(b), have been stored in the temporary register. If no values have been stored in the register, possibly the initial pressure of the occlusion bladder 10 was lower than the systolic pressure of the patient, and steps 77–84 repeat. If values of static pressure have been stored in the register, the microprocessor 28 finds the smallest of these values at step 86. At step 87, the microprocessor 28 relates the smallest value of static pressure to an occlusion pressure value. FIG. 3(b) shows the smallest stored static pressure value at 42. FIG. 3(f) shows the corresponding occlusion pressure value at 48. The value of the occlusion pressure 48 is equal to systolic pressure.

At step 88 of FIG. 5(b), the microprocessor 28 defines a region 54 of the static pressure curve of FIG. 3(b) in which mean arterial pressure is found. At step 89, the microprocessor 28 examines the third derivative curve of FIG. 3(e) for positive-going, zero-crosses, for instance. The microprocessor 28 then stores negative values of the second derivative of the static pressure curve, which correspond to these zero-crosses, in another temporary register. For example, the third derivative of FIG. 3(e) shows two positive-going, zero-crosses 58 and 59. Values 60 and 61 of the second derivative of FIG. 3(d) correspond to the zero-crosses 58 and 59. These values 60 and 61 of the second derivative of FIG. 3(d) are stored in the temporary register.

At step 90, the microprocessor 28 examines the temporary register to see if any negative values of the second derivative are present. If not, at step 93, the microprocessor 28 repeats steps illustrated in FIGS. 5(a) nd 5(b) from step 77. If values are present in the temporary register, the most negative value in the temporary register is found by the microprocessor 28 at step 91. An occlusion pressure value that corresponds to this most negative value in the register is equal to mean arterial pressure. For instance, FIG. 3(d) shows the most negative value at 61. The corresponding occlusion pressure value is 52 in FIG. 3(f), which is the mean arterial pressure of the patient.

If the second derivative of FIG. 4(d), for instance, has two equal most negative values 68 and 69, the microprocessor 28 averages their corresponding occlusion pressure values 70 and 71 at step 94. An average of the occlusion pressure values 70 and 71 yields occlusion pressure value at 52, which is equal to mean arterial pressure. At step 93, the microprocessor 28 derives diastolic pressure in light of the mean arterial pressure and systolic pressures. Diastolic pressure equals $\frac{1}{2}$(3·mean arterial pressure-systolic pressure).

The microprocessor 28 of this invention comprises an INTEL microprocessor, Model Nos. 8088 or 8086, for instance. Code for the microprocessor has been written on a word processor in ASCII format and assembled by an INTEL ASM86 assembler. Resulting hexidecimal code from the assembler is then programmed into an erasable, programmable, read-only memory. The erasable, programmable, read only memory is used by the microprocessor 28 to relate the occlusion pressure curve, static pressure curve, and first, second, and third time derivatives of the static pressure curve. The code is attached as an Appendix.

The invention improves the accuracy of a blood pressure measurement system. The invention recognizes the effects of slow, large noise signal on the system, and filters out those effects to yield an accurate measurement of blood pressure.

APPENDIX

```
msur4B:   CMP offlg,0F8H    ;DEFLATING DONE ?
          JNE sys0          ;NO
          JMP sysok         ;YES sys0:     CMP sclflg,0F8H   ;SYSTOLIC FLAG SET ?
          JE sys1           ;YES
          JMP msur4C        ;NO sys1:     MOV sclflg,000    ;CLEAR SYSTOLIC FLAG
          MOV AX,mlcntr-1
          SHR AX,01
          ADD AX,01
          ADD AX,fsmtmp
          SHL AX,01
          MOV BX,OFFSET fstab
          ADD BX,AX
          MOV AX,DS:[BX]    ;GET SENSE PRESSURE VALUE
          CMP AX,systmp     ;COMPARE VALUE WITH LAST VALUE
          JS sys2           ;JUMP IF NEW VALUE IS LESS
          JMP msur4C        ;THAN LAST VALUE sys2:     MOV systmp,AX     ;PUT NEW VALUE IN LAST VALUE REGISTER
          MOV maxadr,00     ;CLEAR BOUNDARY ADDRESS MOV CX,00
sys3:     INC CX
          CMP CX,010H
          JNS sys4
          SUB BX,02
          MOV AX,DS:[BX]
          SUB AX,01
          CMP AX,systmp     ;FIND BEGINNING OF MINIMUM PLATEAU
          JS sys3 sys4:     MOV AX,fsmtmp
          SUB AX,CX
          MOV fsmtmp,AX

MOV AX,m0cntr-1   ;GET OCCLUSION TABLE POSITION
          ADD AX,mlcntr-1   ;OF SYSTOLIC
          SUB AX,mopcntr-1
          SHR AX,1
          ADD AX,fsmtmp
          ADD AX,01
          SHL AX,01
          MOV BX,OFFSET fotab
          ADD BX,AX
          MOV syspos,BX
```

```
                MOV AX,fotabadr
                SUB AX,02
                CMP AX,BX
                JL syserr
                JMP msur4C sysok:      CMP sclcdn,0F8H   ;IS SYSTOLIC CALC FLAG SET ?
                JNE sysok2        ;YES
                JMP msur4C        ;NO sysok2:     CMP syspos,00
                JE syserr
                MOV BX,syspos
                MOV AX,DS:[BX]    ;CALCULATE SYSTOLIC PRESSURE
                SUB AX,opzero     ;FROM OCCLUSION PRESSURE TABLE
                MOV CX,03E8H
                MOV DX,000
                MUL CX
                DIV opalpha
                SHL DX,01
                CMP DX,opalpha
                JL sok
                ADD AX,01
    sok:        MOV psys,AX       ;SAVE SYS FOR LATER
                MOV rsys,AL       ;AND STORE MOV digstr,AX     ;CVRT SYS HEX TO DEC
                CALL hexdec
                MOV DX,digstr
                MOV BX,OFFSET dspbuf+2
                MOV chrcnt,03
                CALL dspelfl      ;DSPLY LO NIBBLE
                MOV sclcdn,0F8H
                JMP msur4C syserr:     CMP pwrflg,0F8H
                JNE syserB
                JMP syer syserB:     CMP optstr,240                    ;2ND RUN?
                JNE syserA                        ;NO
                JMP syer                          ;YES syserA:     MOV optstr,240                    ;SET UP AUTO RE-INFLATE
                MOV opt,240                       ;SINCE NO SYSTOLIC
                MOV offlg,00
                MOV sclflg,00
                MOV mclflg,00
                MOV mapflg,00
                MOV mpdone,00
                MOV dacrun,0F8H   ;SET DAC1 TO FOLLOW
                MOV oiflg,0F8H    ;SET UP OCC INT VAL
                MOV bpflg,0F8H    ;SET UP BP INT VALS
                MOV hrflg,0F8H    ;SET UP HR INT VALS
                CMP hlpflg,0F8H   ;HELP ON
                JNE nc0a          ;NO
```

```
              MOV DX,0ACBH        ;YES,DSPLY HElp
              MOV BX,OFFSET dspbuf+2
              MOV chrcnt,03
              CALL dspelfl MOV DX,0DEAH        ;DSPLY heLP
              MOV BX,OFFSET dspbuf+2
              MOV chrcnt,03
              CALL dspelfh
              JMP nc0b            ;NO PUMP nc0a:   MOV AL,010H         ;PUMP ON
              MOV DX,pump
              OUT DX,AL nc0b:   MOV AX,0800H
      nc0c:   DEC AX
              JNZ nc0c OR run,050H         ;RSTRT OC INF & BP
              MOV t50ovr,00
              JMP msurF           ;ALL ON NEXT PASS syer:   MOV rsys,0FFH       ;SECOND TRY ALSO NO SYSTOLIC
              MOV rmap,0FFH       ;DISPLAY ERROR
              MOV rdys,0FFH MOV DX,0FBFH                ; E
              MOV BX,OFFSET dspbuf+2
              MOV chrcnt,03
              CALL dspelfl        ;DSPLY LO NIBBLE MOV DX,0FBFH                ; E
              MOV BX,OFFSET dspbuf+2
              MOV chrcnt,03
              CALL dspelfh        ;DSPLY HI NIBBLE MOV DX,0FBFH                ; E
              MOV BX,OFFSET dspbuf+5
              MOV chrcnt,03
              CALL dspelfl        ;DSPLY LO NIBBLE
              JMP bpr20           ;STOP BP,STRT HR msur4C:  CMP mclflg,0F8H             ;MAP CALC FLAG SET ?
              JE map1                     ;YES
              JMP msur5                   ;NO map1:    MOV mclflg,000

MOV mpdone,0F8H
     OR run,04H                   ;STRT HR RUN
     MOV hrflg,0F8H               ;HR 1ST PASS MOV AX,m0cntr-1              ;CALCULATE MAP POSITION
     ADD AX,m1cntr-1              ;ON OCCLUSION TABLE
```

```
        ADD AX,m2cntr-1
        ADD AX,m3cntr-1
        ADD AX,m4cntr-1
        SUB AX,mopcntr-1
        SHR AX,1
        ADD AX,map3d
        ADD AX,03
        SHL AX,1
        MOV BX,OFFSET fotab
        ADD BX,AX
        MOV mappos,BX MOV AX,m0cntr-1         ;CALCULATE MAP FROM
        SHR AX,01               ;TABLE POSTION
        MOV CX,mopcntr-1
        SHR CX,01
        MOV BX,maxadr
        ADD BX,AX
        SUB BX,CX
        MOV CX,m1cntr-1
        SHR CX,01
        ADD BX,CX
        ADD BX,01
        SHL BX,01
        ADD BX,OFFSET fotab
        MOV AX,DS:[BX]
        MOV CX,opzero
        SUB AX,CX
        MOV CX,03E8H
        MOV DX,00
        MUL CX
        DIV opalpha
        MOV diast,AX            ;ESTIMATE DIASTOLIC MOV BX,mappos
        MOV AX,fotabadr
        SUB AX,02
        CMP BX,AX               ;MAP POSITION IN CORRECT PART
                                   OF TABLE ?
        JL mapok1               ;YES,OK
        JMP bpr19               ;NO,STOP BP STRT HR mapok1: MOV CX,syspos           ;MAP < SYSTOLIC ?
        CMP mappos,CX
        JG mapok2               ;YES,OK
        JMP maper1              ;NO,STOP BP STRT HR mapok2: MOV AX,DS:[BX]          ;CALCULATE MAP
        MOV CX,opzero
        SUB AX,CX
        MOV CX,03E8H
        MOV DX,000
        MUL CX
        DIV opalpha
        SHL DX,01
```

```
              CMP DX,opalpha
              JL mok
              ADD AX,01
   mok:       SUB AX,mapfdg
              MOV pmap,AX              ;SAVE MAP
              MOV rmap,AL              ;AND STORE MOV DX,000               ;CALCULATE DIASTOLIC
              MOV CX,003
              MUL CX
              SUB AX,psys
              JNS mapok3
              MOV AX,00
   mapok3:    MOV DX,00
              MOV CX,002
              DIV CX                   ;AX HOLDS DIASTOLIC
              MOV pdys,AX              ;SAVE DIASTOLIC
              MOV rdys,AL              ;AND STORE SUB AX,diast
              CMP AX,00
              JNS mapok4
              CMP AX,0FFF4H
              JG mapok4
   maper1:    MOV BX,diast
              MOV pdys,BX
              MOV rdys,BL
              MOV AX,psys
              SUB AX,BX
              MOV DX,00
              MOV CX,03
              DIV CX
              ADD AX,BX
              MOV pmap,AX
              MOV rmap,AL
              OR rcal,03H
              MOV flshflg,0F8H         ;STARTS FLASHING DISPLAY
              MOV flshdec,020          ;IF ESTIMATION OCCURED mapok4:    MOV AX,pdys
              MOV digstr,AX            ;CONVERT DIASTOLIC FOR DISPLAY
              CALL hexdec
              MOV DX,digstr
              MOV BX,OFFSET dspbuf+2
              MOV chrcnt,03
              CALL dspelfh             ;DSPLY HI NIBBLE MOV AX,pmap
              MOV digstr,AX            ;CONVERT MAP FOR DISPLAY
              CALL hexdec
              MOV DX,digstr
              MOV BX,OFFSET dspbuf+5
              MOV chrcnt,03
              CALL dspelfl             ;DSPLY LO NIBBLE
              CMP flshflg,0F8H
```

```
                JNE     mapok5
                MOV     BX,OFFSET dspbuf+010
                MOV     CX,03
mapok6:         MOV     AL,DS:[BX]
                AND     AL,0FH
                OR      AL,0F0H
                MOV     DS:[BX],AL
                ADD     BX,03
                MOV     AL,DS:[BX]
                AND     AL,0F0H
                OR      AL,0FH
                MOV     DS:[BX],AL
                SUB     BX,04
                LOOP    mapok6 mapok5:         AND     strdat,0F7H             ;BIT 3 OFF
                AND     run,0BFH                ;STOP BP msur7:          TEST    run,001H                ;MEASURE SENSE INFLATION ?
                JNZ     snc                     ;YES
                JMP     msur8                   ;NO snc:            CMP     stflg,0F8H              ;1ST PASS ?
                JE      snc0                    ;YES
                JMP     snc1                    ;NO snc0:           MOV     stflg,000               ;SET UP FOR SENSE
                MOV     spdone,000              ;0 DONE FLAG
                MOV     spnctr,000              ;0 CNTR
                MOV     splcnt,spl cnt          ;LOAD SMPS#
                MOV     spltbl,000              ;ZERO SUM REG
                MOV     AL,010H                 ;SETUP & START
                MOV     DX,v1
                OUT     DX,AL                   ;V1/V2 CLOSED CMP     hlpflg,0F8H             ;HELP ON
                JNE     snc0a                   ;NO MOV     DX,0ACBH                ;YES,DSPLY HElp
                MOV     BX,OFFSET dspbuf+2
                MOV     chrcnt,03
                CALL    dspelfl MOV     DX,0DEAH                ;DSPLY heLP
                MOV     BX,OFFSET dspbuf+2
                MOV     chrcnt,03
                CALL    dspelfh
                JMP     snc0b                   ;NO PUMP snc0a:          CMP     fcdstr,0F8H
                JNE     snc0d
                MOV     fcdtmp,0F8H
                MOV     DX,fcd
                MOV     AL,00
                OUT     DX,AL
```

```
snc0d:   MOV AL,010H              ;PUMP ON
         MOV DX,pump
         OUT DX,AL                ;PUMP ON snc0b:   MOV DX,0                 ;CALC RATE
         MOV AX,014H
         MUL spalpha
         MOV CX,03E8H
         DIV CX
         ADD AX,spzero
         MOV sptest,AX MOV DX,0                 ;CALC SET VALUE
         MOV AX,05AH
         MUL spalpha
         MOV CX,03E8H
         DIV CX
         ADD AX,spzero
         MOV spstop,AX
         JMP msur8 snc1:    MOV BX,OFFSET adctbl+2   ;DO SENSE INFLATE
         MOV AX,DS:[BX]           ;GET DATA
         ADD sp1tbl,AX            ;SUM IT
         DEC sp1ent               ;ALL SMPS IN
         JZ snc1c                 ;YES
         JMP msur8                ;NO snc1c:   MOV CL,sp1shft           ;GET DIV #
         MOV AX,sp1tbl            ;GET SUM
         SHR AX,CL                ;AVRG IT
         MOV sp1str,AX            ;SAVE
         MOV sp1ent,sp1cnt        ;RLD SMPS#
         MOV sp1tbl,000           ;ZERO SUM REG INC spnctr               ;INFLATE SENSE
         CMP AX,spstop            ;AT SET VALUE
         JL snc2                  ;NO,KEEP GOING MOV DX,ds1               ;YES,SET DS1 TO 1
         MOV AL,010H
         OUT DX,AL
         MOV AL,010H              ;YES,SWITCH V3
         MOV DX,v3
         OUT DX,AL
         MOV stflg,0F8H           ;SET 1ST PASS AND
         MOV spdone,0F8H          ;SET TO INIT OCCL
         MOV ampdn,000
         AND run,0FEH             ;STOP SENSE INFLATE
         JMP msur8                ;AND BP MEASURE VALS snc2:    CMP spnctr,032H
         JG snc3
         JMP msur8
```

```
snc3:    MOV AX,sp1str
         CMP AX,sptest           ;INFLATION RATE OK
         JNG snc4                ;NO
         CMP spnctr,064H         ;INFLATION TIME OK
         JG snc4                 ;NO
         JMP msur8 snc4:    MOV stflg,000           ;STOP RUN, ERROR
         MOV AL,000
         MOV DX,pump
         OUT DX,AL               ;PUMP OFF
         MOV DX,v1
         OUT DX,AL               ;V1/V2 OFF
         MOV DX,v3
         OUT DX,AL               ;V3 OPEN
         MOV stflg,0F8H
         AND run,022H            ;BP,HR,INFLS OFF
         MOV chkflg,07H          ;SENSE CUFF ERROR msur8:   TEST run,010H           ;DO OCCL UP/DWN ?
         JNZ occa                ;YES
         JMP msur9               ;NO occa:    CMP oiflg,0F8H          ;1ST PASS ?
         JE occs                 ;YES
         JMP occ                 ;NO occs:    MOV oiflg,000           ;1ST DONE
         MOV opnctr,000          ;ZERO FLAGS
         MOV oprctr,00
         MOV odflg,000           ;SET UP TABLES
         MOV tglflg,0F8H         ;SET VALVE TOGGLE
         MOV sclcdn,000          ;FOR BLEED
         MOV opuptim,04AH        ;SET INFLATE TIME
         MOV BX,OFFSET opitbl    ;RESET DATA
         MOV rotabadr,BX         ;TABLE BASE
         MOV rohld,BX
         MOV BX,OFFSET fotab     ;FILTER DATA
         MOV fotabadr,BX         ;TABLE BASE
         MOV AX,000              ;ZERO
         MOV op1ent,op1cnt       ;RELOAD SMPS #
         MOV op1sum,000          ;ZERO SUM REG
         MOV offlg,00 occs0:   MOV AX,opalpha          ;CALC STOP VALUE
         MOV DX,00
         MUL opt
         MOV CX,03E8H
         DIV CX
         ADD AX,opzero
         MOV opstop,AX SUB AX,opzero           ;SET UP SPD
         MOV DX,00
         MOV CX,0100H
         MUL CX
```

```
         MOV CX,opuptim          ;# -> SPD
         DIV CX
         MOV opr256,AX MOV AX,opstop           ;SET DWN SPD
         SUB AX,opzero
         MOV DX,00
         MOV CX,0100H
         MUL CX
         MOV CX,opdntim          ;# VARYS SPD
         DIV CX
         CMP opt,240
         JNE occs1
         MOV CX,029BH
         MUL CX
         MOV CX,03E8H
         DIV CX
occs1:   MOV opr256d,AX
         JMP msur9 occ:     CMP spdone,0F8H         ;SENSE DONE?
         JE occ0                 ;YES
         JMP msur9               ;NO, NOT YET occ0:    MOV BX,OFFSET adctbl+04 ;DO OC INFL
         MOV AX,DS:[BX]          ;GET DATA
         ADD op1sum,AX           ;SUM IT
         DEC op1ent              ;ALL SMPS IN
         JZ occ1                 ;YES
         JMP msur9               ;NO
occ1:    MOV CL,op1shft          ;GET DIV #
         MOV AX,op1sum           ;GET SUM
         SHR AX,CL               ;AVRG IT
         MOV op1str,AX           ;SAVE
         MOV op1ent,op1cnt       ;RLD SMPS #
         MOV op1sum,000          ;ZRO SUM REG
         INC oprctr CMP AX,opzero
         JGE occ2
         JMP msur9 occ2:    CMP mpdone,0F8H         ;MAP IN
         JE occ3                 ;YES,NO OCCL DSPLY SUB AX,opzero           ;NO,CALC OCCL VAL
         MOV CX,03E8H            ;FOR DSPLY
         MOV DX,000
         MUL CX
         DIV opalpha MOV digstr,AX           ;CNVRT OCC HEX TO DEC
         CALL hexdec
         MOV BX,OFFSET dspbuf+5
         MOV DX,digstr
         MOV chrcnt,03
         CALL dspelfl            ;DSPLY LO NIBBLE
```

```
occ3:    CMP odflg,0F8H           ;START DATA TAKING ?
         JE occ3a                 ;YES
         JMP occ4                 ;NO, WAIT occ3a:   MOV AX,op1str
         MOV BX,rotabadr          ;PUT IN TBL
         MOV DS:[BX],AX
         ADD BX,02                ;LD NEXT ADR
         MOV rotabadr,BX
         INC opnctr CMP opnctr,mopcntr       ;FILTER?
         JGE occ3b                ;YES
         JMP occ4                 ;NO occ3b:   MOV fncntr,mopcntr       ;DO FLTR RTN
         MOV BX,rohld
         MOV tsain,BX
         ADD BX,02
         MOV rohld,BX
         MOV BX,fotabadr
         MOV tsaout,BX
         CALL maf
         MOV BX,tsaout
         MOV fotabadr,BX occ4:    CMP odflg,0F8H           ;DEFLATE
         JNE occ5                 ;NO
         JMP occ10                ;YES occ5:    MOV AX,op1str
         CMP AX,opstop            ;OP1>OPSTOP?
         JNG occ6                 ;NO MOV DX,0FFFH             ;CLEAR HELP
         MOV BX,OFFSET dspbuf+2
         MOV chrcnt,03
         CALL dspelfl
         MOV DX,0FFFH
         MOV BX,OFFSET dspbuf+2
         MOV chrcnt,03
         CALL dspelfh MOV AX,000
         MOV DX,pump
         OUT DX,AL                ;STOP PUMP occ5a:   MOV tglflg,00            ;STOP TOGGLE MOV DX,v1
         MOV AL,010H
         OUT DX,AL                ;CLOSE V1/V2

MOV odflg,0F8H           ;YES, START DEFLATE
         MOV AX,fotabadr          ;GET CURRENT FO ADR
         SUB AX,02                ;AND SAVE FOR PRN
         MOV odadr,AX
```

```
            MOV AX,odadr              ;SAVE ODFLG ADDR
            MOV btemp,AX              ;FOR PRNT OUT MOV ocwt,060              ;SET 7 SEC WAIT
            MOV AX,oprctr
            ADD AX,ocwt
            MOV opuptim1,AX JMP msur9                 ;STRT DEFL IF DONE occ6:       MOV AX,opr256
            MUL oprctr
            MOV CX,0100H
            DIV CX
            ADD AX,opzero             ;(OPR256*OPNCTR
            MOV opt,AX                ;/0100H)+OPZERO
            CMP op1str,AX             ;OP1 > OPT ?
            JNG occ7                  ;NO
            JMP msur9                 ;YES occ7:       MOV AX,opt
            SHR AX,1                  ;OPT/2
            CMP op1str,AX             ;OPSTR > OPT/2 ?
            JNG occ9                  ;NO
            JMP msur9                 ;YES occ9:       CMP oprctr,01C2H
            JG occ9a                  ;NO
            JMP msur9                 ;YES occ9a:      JMP operr occ10:      DEC ocwt                  ;DEC WAIT TIME
            JZ occ10a                 ;WAIT OVER
            JMP msur9                 ;NOT OVER occ10a:     MOV ocwt,01
            MOV tglflg,0F8H           ;TOGGLE
            MOV AX,0A0H               ;10 mmHg
            ADD AX,opzero
            CMP op1str,AX             ;OP1<ZERO+10 ?
            JNS occ11                 ;NO MOV BX,fotabadr           ;YES
            SUB BX,02
            MOV CX,DS:[BX]
            CMP CX,AX                 ;LESS THAN CUTOFF
            JGE occ11                 ;NO
            AND run,0EFH              ;YES,STOP I/D OCCL MOV offlg,0F8H
            CMP syspos,00
            JNE rnend
            JMP syserr                ;NO rnend:      MOV AL,00
            MOV DX,v1
```

```
              OUT DX,AL
              JMP msur9 occ11:        MOV BX,fotabadr              ;GET LATEST FILT OCCL
              SUB BX,02
              MOV CX,DS:[BX]
              MOV AX,0280H
              ADD AX,opzero
              CMP CX,AX                    ;LESS THAN CUTOFF
              JGE occ11a
              CMP syspos,00
              JNE occ11a
              JMP syserr occ11a:       CMP oprctr,03E8H             ;>100 SECS
              JNG occ12                    ;NO
              JMP operr                    ;YES occ12:        MOV AX,oprctr
              SUB AX,opuptim1              ;OPNCTR-OPUPTIM1=OPT
              MOV DX,00
              MUL opr256d                  ;OPT*OPR256D/100H
              MOV CX,0100H
              DIV CX
              MOV BX,AX                    ;OPT IN BX
              MOV AX,opstop
              SUB AX,BX
              MOV opt,AX
              JMP msur9 operr:        AND run,022H                 ;YES,OIDFLG = 0
              MOV AL,000                   ;PUMP OFF
              MOV DX,pump
              OUT DX,AL
              MOV DX,v1                    ;EXHAUST OPEN
              OUT DX,AL
              MOV DX,v3                    ;SENSE OPEN
              OUT DX,AL
              MOV DX,ds1                   ;DS1 TO 0
              OUT DX,AL
              MOV dacrun,000               ;STOP DAC SERVO
              MOV AL,000
              MOV DX,dac1                  ;ZERO DAC 1 & 2
              OUT DX,AL
              MOV DX,dac2
              OUT DX,AL
              MOV spdone,000
              MOV chkflg,06H               ;SET PNEUMATIC ERROR msur9:        TEST run,040H                ;MEASURE BLD PRESS ?
              JNZ bpr0                     ;YES
              JMP msurA                    ;NO bpr0:         CMP bpflg,0F8H               ;1ST PASS
              JE bprs                      ;YES
              JMP bpr1                     ;NO
```

```
bprs:   MOV bpflg,000
        MOV fsdctr,00          ;SET UP BP INIT VALS
        MOV fsfctr,00
        MOV fsnctr,00
        MOV fsmctr,00
        MOV fsmtmp,00
        MOV fslctr,00
        MOV fsoctr,00
        MOV fssctr,00
        MOV mapflg,00
        MOV mpdone,00
        MOV sclcdn,00
        MOV mappos,00
        MOV syspos,00
        MOV pmap,00
        MOV psys,00
        MOV pdys,00
        MOV sclflg,00
        MOV mclflg,00
        MOV map2d,0FFFDH
        MOV map3d,00
        MOV systmp,0FFFH
        MOV fsomin,00
        MOV fsomax,00
        MOV maxadr,00
        MOV AX,0AH
        MOV DX,00
        MOV CX,opalpha
        MUL CX
        MOV CX,03E8H
        DIV CX
        MOV mapmin,AX
        MOV AX,m0cntr-1
        ADD AX,m1cntr-1
        SHR AX,01
        ADD AX,01
        ADD AX,spdly
        MOV fssctr,AX MOV sp4ent,sp4cnt      ;RLD SMFS #
        MOV sp4sum,000         ;ZRO SUM REG
        MOV BX,OFFSET sp4tbl
        MOV rstabadr,BX
        MOV rshld,BX
        MOV BX,OFFSET fstab
        MOV fstabadr,BX
        MOV BX,OFFSET s1dtab   ;DERIVATIVE
        MOV s1dtabadr,BX       ;TABLES
        MOV s1hld,BX
        MOV BX,OFFSET f1dtab
        MOV f1dtabadr,BX
        MOV BX,OFFSET s2dtab
        MOV s2dtabadr,BX
        MOV s2hld,BX
        MOV BX,OFFSET f2dtab
        MOV f2dtabadr,BX
        MOV BX,OFFSET s3dtab
        MOV s3dtabadr,BX
```

```
            MOV  s3hld,BX
            MOV  BX,OFFSET f3dtab
            MOV  f3dtabadr,BX
            MOV  BX,OFFSET f4dtab
            MOV  s4hld,BX
            MOV  f4tabadr,BX
            MOV  f4dtabadr,BX
            JMP  msurA bpr1:     CMP  odflg,0F8H          ;DEFLATING?
            JE   bpr1a               ;YES,DO BP
            JMP  msurA               ;NOT YET bpr1a:    CMP  sclcdn,0F8H
            JNE  bpr1b
            JMP  bpr16 bpr1b:    MOV  BX,OFFSET adctbl+0EH
            MOV  AX,DS:[BX]          ;GET SP4 DATA
            ADD  sp4sum,AX           ;SUM IT
            DEC  sp4ent              ;ALL SMPS IN
            JZ   bpclc               ;YES
            JMP  msurA               ;NO bpclc:    MOV  CL,sp4shft          ;GET DIV #
            MOV  AX,sp4sum           ;GET SUM
            SHR  AX,CL               ;AVRG IT
            MOV  sp4str,AX           ;SAVE
            MOV  sp4ent,sp4cnt       ;RLD SMPS #
            MOV  sp4sum,000          ;ZRO SUM REG bpr2:     MOV  CX,opnctr           ;GET CNTR VALUE
            CMP  CX,spdly            ;OPTBLCTR >= SPDLY
            JGE  bpr3                ;YES
            JMP  msurA               ;NO,WAIT bpr3:     MOV  AX,sp4str
            MOV  BX,rstabadr         ;STORE IN TABLE
            MOV  DS:[BX],AX
            ADD  BX,02               ;LOAD NEXT ADDR
            MOV  rstabadr,BX
            INC  fsdctr MOV  AX,OFFSET sp4tbl+440H
            CMP  BX,AX               ;OUT OF TABLE SPACE?
            JNG  bpr4                ;NO
            JMP  syserr              ;YES,DSPLY EEE bpr4:     CMP  sp4str,0200H
            JLE  bpr7A CMP  sp4str,0FFFH
            JL   bpr7B bpr7A:    MOV  chkflg,03           ;SENSE OUT OF
            JMP  msurA               ;RANGE ERROR
```

```
bpr7B:     CMP  fsdctr,m0cntr        ;>M0CNTR ?
           JGE  bpr5                 ;YES
           JMP  msurA                ;NO bpr5:      MOV  fncntr,m0cntr        ;FILTER
           MOV  BX,rshld
           MOV  tsain,BX
           ADD  BX,02
           MOV  rshld,BX
           MOV  BX,fstabadr
           MOV  tsaout,BX
           CALL maf
           MOV  BX,tsaout
           MOV  fstabadr,BX
           INC  fsnctr bpr5c:     CMP  fsnctr,01            ;FSNCTR > 1
           JG   bpr5b                ;YES
           JMP  msurA                ;NO bpr5b:     MOV  BX,fstabadr
           SUB  BX,02
           MOV  AX,DS:[BX]           ;GET CURRENT DATA
           SUB  BX,02
           MOV  CX,DS:[BX]           ;GET PREVIOUS DATA
           SUB  AX,CX                ;CURRENT- PREVIOUS
           MOV  CX,m1mul
           MUL  CX
           MOV  BX,s1dtabadr
           MOV  DS:[BX],AX           ;STORE UNFILT 1ST D
           ADD  BX,02
           MOV  s1dtabadr,BX CMP  fsnctr,m1cntr+1      ;>=M1CNTR?
           JGE  bpr8                 ;YES
           JMP  msurA bpr8:      MOV  fncntr,m1cntr        ;FILTER
           MOV  BX,s1hld
           MOV  tsain,BX
           ADD  BX,02
           MOV  s1hld,BX
           MOV  BX,f1dtabadr
           MOV  tsaout,BX
           CALL maf
           MOV  BX,tsaout
           MOV  f1dtabadr,BX
           INC  fsmctr
           CMP  maxadr,00
           JNE  bpr8c
           MOV  BX,f1dtabadr
           SUB  BX,04
           MOV  AX,DS:[BX]
           CMP  AX,00
           JS   bpr8c
           ADD  BX,02
           MOV  AX,DS:[BX]
```

```
            CMP AX,00
            JNS bpr8c
            MOV AX,fsmctr
            MOV maxadr,AX bpr8c:      MOV CL,m4shft              ;FILTER AGAIN
            CMP CL,00
            JE bpr8b
            SUB BX,02
            MOV AX,DS:[BX]
            SHL AX,CL
            MOV BX,f4tabadr
            MOV DS:[BX],AX
            ADD BX,02
            MOV f4tabadr,BX
bpr8b:      CMP fsmctr,m4cntr
            JGE bpr8a
            JMP msurA bpr8a:      MOV fncntr,m4cntr          ;FILTER
            MOV BX,s4hld
            MOV tsain,BX
            ADD BX,02
            MOV s4hld,BX
            MOV BX,f4dtabadr
            MOV tsaout,BX
            CALL maf
            MOV BX,tsaout
            MOV f4dtabadr,BX
            INC fsfctr CMP fsfctr,01              ;OK TO PROCEED ?
            JG bpr9                    ;YES
            JMP msurA                  ;NO bpr9:       MOV BX,f4dtabadr
            SUB BX,2
            MOV AX,DS:[BX]             ;GET CURR FLTRD 1D
            SUB BX,2
            MOV DX,DS:[BX]             ;GET PREV FLTRD 1D
            SUB AX,DX
            MOV CX,m2mul
            MUL CX
            MOV BX,s2dtabadr
            MOV DS:[BX],AX             ;SAVE UNFILT 2D
            ADD BX,02
            MOV s2dtabadr,BX           ;AND STORE NEXT ADDR CMP fsfctr,m2cntr+1        ;>=M2CNTR   ?
            JGE bpr10                  ;YES
            JMP msurA                  ;NO bpr10:      MOV fncntr,m2cntr          ;FILTER
            MOV BX,s2hld
            MOV tsain,BX
            ADD BX,02
            MOV s2hld,BX
```

```
           MOV BX,f2dtabadr
           MOV tsaout,BX
           CALL maf
           MOV BX,tsaout
           MOV f2dtabadr,BX bpr10c:    INC fslctr
           CMP fslctr,01              ;FSLCTR > 1 ?
           JG bpr11                   ;YES
           JMP msurA                  ;NO bpr11:     MOV BX,f2dtabadr
           SUB BX,2
           MOV AX,DS:[BX]             ;GET CURR FLTRD 2D
           SUB BX,2
           MOV DX,DS:[BX]             ;GET PREV FLTRD 2D
           SUB AX,DX
           MOV CX,m3mul
           MUL CX
           MOV BX,s3dtabadr
           MOV DS:[BX],AX             ;SAVE UNFILT 3D
           ADD BX,02
           MOV s3dtabadr,BX           ;AND STORE NEXT ADDR
           CMP fslctr,m3cntr+1        ;>=M3CNTR ?
           JGE bpr12                  ;YES
           JMP msurA                  ;NO bpr12:     MOV fncntr,m3cntr          ;FILTER
           MOV BX,s3hld
           MOV tsain,BX
           ADD BX,02
           MOV s3hld,BX
           MOV BX,f3dtabadr
           MOV tsaout,BX
           CALL maf
           MOV BX,tsaout
           MOV f3dtabadr,BX
           INC fsoctr bpr13:     MOV AX,fsmctr
           CMP AX,fssctr              ;FSDCTR>FSSCTR?
           JG bpr13A                  ;YES
           JMP msurA bpr13A:    CMP mpdone,0F8H            ;MAP IN ?
           JNE bpr14                  ;NO
           JMP msurA                  ;YES bpr14:     CMP fsmtmp,000             ;SYSTOLIC IN REGISTER ?
           JE bpr14A
           MOV BX,f1dtabadr           ;NO
           SUB BX,02                  ;LOOK FOR IT
           MOV AX,DS:[BX]             ;GET CURRENT F1D
           CMP AX,08
           JL bpr14A
           JMP sysclc
```

```
bpr14A:  MOV  BX,f1dtabadr        ;NO
         SUB  BX,04               ;LOOK FOR IT
         MOV  AX,DS:[BX]          ;GET CURRENT F1D-1
         CMP  AX,00               ;F1D-1<0
         JS   bpr15               ;YES
         JMP  msurA               ;NO bpr15:   ADD  BX,2
         MOV  AX,DS:[BX]          ;GET CURRENT F1D
         CMP  AX,00               ;F1D>=0
         JNS  bpr15a              ;GOT 0 CROSS,DO SYS
         JMP  msurA               ;NO CROSS bpr15a:  JMP  bpr18               ;DO SYSTOLIC COMPARISON bpr16:   CMP  mpdone,0F8H         ;MAP TIME ?
         JNE  bpr16z              ;YES
         JMP  msurA bpr16z:  MOV  BX,syspos
         MOV  AX,DS:[BX]
         SUB  AX,mapmin bpr16a:  ADD  BX,02               ;DEFINE RANGE FOR MAP
         MOV  CX,DS:[BX]
         CMP  CX,AX
         JG   bpr16a
         SUB  BX,OFFSET fotab
         SHR  BX,01
         SUB  BX,03
         MOV  AX,m0cntr-1
         ADD  AX,m1cntr-1
         ADD  AX,m2cntr-1
         ADD  AX,m3cntr-1
         ADD  AX,m4cntr-1
         SUB  AX,mopcntr-1
         SHR  AX,01
         SUB  BX,AX
         MOV  fsomin,BX MOV  AX,m2cntr-1
         ADD  AX,m3cntr-1
         ADD  AX,m4cntr-1
         SHR  AX,01
         ADD  AX,02
         MOV  BX,maxadr
         SUB  BX,AX
         SUB  BX,04
         MOV  fsomax,BX
         CMP  BX,fsomin
         JG   bpr16b
         JMP  bpr19 bpr16b:  MOV  AX,fsoctr
         CMP  BX,AX
         JL   bpr16m
         MOV  fsomax,AX
```

```
bpr16m: MOV map2d,OFFFDH          ;START REVIEWING 3D
        MOV map3d,00              ;FOR POSSIBLE MAPS
        MOV CX,fsomin
        SUB CX,01 bpr16c: INC CX
        CMP CX,fsomax
        JS bpr16n
        JMP mapclc bpr16n: MOV AX,m3cntr-1
        SHR AX,01
        ADD AX,CX
        ADD AX,01
        SHL AX,01
        MOV BX,OFFSET f2dtab
        ADD BX,AX
        MOV AX,DS:[BX]
        CMP AX,00
        JS bpr16d
        JMP bpr16c bpr16d: MOV BX,CX
        SHL BX,01
        ADD BX,OFFSET f3dtab
        SUB BX,02
        MOV AX,DS:[BX]
        CMP AX,00
        JS bpr16e
        JMP bpr16c bpr16e: ADD BX,02                 ;CHECK FOR ZERO CROSS
        MOV AX,DS:[BX]
        CMP AX,00
        JNS bpr16f
        JMP bpr16c bpr16f: MOV AX,m3cntr-1           ;GOT ZERO CROSS
        SHR AX,01
        ADD AX,CX
        ADD AX,01
        SHL AX,01
        MOV BX,OFFSET f2dtab
        ADD BX,AX
        MOV AX,DS:[BX]
        ADD AX,08
        CMP AX,map2d
        JS bpr16g
        SUB AX,010H
        CMP AX,map2d
        JE bpr16h
        ADD AX,08
        CMP AX,map2d
        JE bpr16h
        ADD AX,08
        CMP AX,map2d              ;CHECK IF 2D MOST NEGATIVE
        JE bpr16h
        JMP bpr16c
```

```
bpr16g:  SUB AX,08                    ;YES, SO SET REGISTERS
         MOV map2d,AX
         MOV map3d,CX
         JMP bpr16c bpr16h:  MOV AX,map3d
         ADD AX,CX
         SHR AX,01
         MOV map3d,AX
         JMP bpr16c bpr18:   MOV AX,fsmctr
         MOV fsmtmp,AX
         JMP msurA bpr19:   CMP opdntim,0138H            ;AUTO RE-INFLATE FOR MAP
         JE bpr19a
         JMP bpr19g
bpr19a:  MOV opdntim,01A0H
         MOV AX,psys
         CMP AX,0200
         JL bpr19e
         MOV opt,0239
         MOV optstr,0239
         JMP bpr19f
bpr19e:  ADD AX,040
         MOV opt,AX
         MOV optstr,AL
bpr19f:  MOV offlg,00
         MOV sclflg,00
         MOV mclflg,00
         MOV mapflg,00
         MOV mpdone,00
         MOV dacrun,0F8H              ;SET DAC1 TO FOLLOW
         MOV oiflg,0F8H               ;SET UP OCC INT VAL
         MOV bpflg,0F8H               ;SET UP BP INT VALS
         MOV hrflg,0F8H               ;SET UP HR INT VALS CMP hlpflg,0F8H              ;HELP ON
         JNE bpr19b                   ;NO MOV DX,0ACBH                 ;YES,DSPLY HElp
         MOV BX,OFFSET dspbuf+2
         MOV chrcnt,03
         CALL dspelfl MOV DX,0DEAH                 ;DSPLY heLP
         MOV BX,OFFSET dspbuf+2
         MOV chrcnt,03
         CALL dspelfh
         JMP bpr19c                   ;NO PUMP bpr19b:  MOV AL,010H                  ;PUMP ON
         MOV DX,pump
         OUT DX,AL
```

```
bpr19c:  MOV  AX,0800H
bpr19d:  DEC  AX
         JNZ  bpr19d

OR   run,050H           ;RSTRT OC INF & BP
         MOV  t50ovr,00
         JMP  msurF              ;ALL ON NEXT PASS bpr19g:  MOV  rmap,0FFH          ;STORE ERROR CODE
         MOV  rdys,0FFH          ;BOTH MAP & DIAS
         MOV  DX,0FBFH           ; E
         MOV  BX,OFFSET dspbuf+2
         MOV  chrcnt,03
         CALL dspelfh            ;DSPLY HI NIBBLE
         MOV  DX,0FBFH           ; E
         MOV  BX,OFFSET dspbuf+5
         MOV  chrcnt,03
         CALL dspelfl            ;DSPLY LO NIBBLE bpr20:   MOV  mpdone,0F8H
         AND  strdat,0F7H        ;BIT 3 OFF
         AND  run,0AFH           ;STOP OC DFLT & BP
         OR   run,04H            ;START HR RUN
         MOV  t50ovr,00
         MOV  hrflg,0F8H         ;SET HR 1ST PASS
         JMP  msurA sysclc:  MOV  sclflg,0F8H        ;SET SYSTOLIC DONE
         JMP  msurA mapclc:  MOV  mclflg,0F8H        ;SET MAP DONE
         MOV  t50ovr,00 msurA:   NOP
```

What is claimed is:

1. A blood pressure measurement system comprising:
an occlusion bladder attachable to an upper portion of a limb;
a sensing bladder attachable to a lower portion of the limb;
a means for monitoring a first pressure in the occlusion bladder and producing an occlusion pressure signal related to the first pressure and for monitoring a second pressure in the sensing bladder and producing a sensing pressure signal related to the second pressure;
a means for filtering out blood pulse signals from the sensing pressure signal and producing a static pressure signal;
a means for recognizing and storing a plurality of relative minimums of the static pressure signal; and
a means for relating the smallest of the relative minimums of the static pressure signal with a corresponding occlusion pressure value to derive systolic pressure.

2. The apparatus of claim 1 comprising;
a means for determining inflection points in the static pressure signal after systolic pressure has occurred;
a means for determining a second derivative of the static pressure signal and magnitudes of the second derivative corresponding to the inflection points;
a means for relating a most negative of these magnitudes of the second derivative with a corresponding occlusion bladder pressure value to derive mean arterial pressure.

3. The system of claim 2, comprising;
a means for deriving first, second, and third derivatives of the static pressure signal;
a means for recognizing positive-going, zero-crosses derivatives of the static pressure signal;
a means for recognizing positive-going, zero-crosses of the first derivative;
a means for storing a static pressure value corresponding to each zero-cross of the first derivative, each static pressure value comprising a relative minimum of the static pressure signal, the smallest of which corresponds to systolic pressure.

4. The system of claim 3, comprising;
a means for determining positive-going, zero-crosses of the third derivative;
a means for storing negative values of the second derivative corresponding to the zero-crosses of the third derivative; and
a means for relating a most negative value of the stored negative values of the second derivative to a corresponding occlusion pressure value to derive mean arterial pressure.

5. The system of claim 4, comprising;
a means for determining if two or more stored negative values are equal, for determining occlusion pressure values corresponding to the two or more equal stored negative values, and for averaging these occlusion pressure values to derive mean arterial pressure.

6. The system of claim 5, comprising;
a means for defining a region of the static pressure signal within which mean arterial pressure occurs, the region beginning with a first static pressure value corresponding to systolic pressure and ending with a maximum static pressure value occurring after the first static pressure value.

7. A system for non-invasive, substantially noise-immune measurement of the blood pressure of a patient, comprising:
first cuff means for occluding blood flow in a limb of the patient;
second cuff means for sensing pressure in the limb and disposed between said first cuff means and the distal end of the limb;
means for monitoring the pressure in said first cuff means;
means for monitoring the pressure in said second cuff means;
means for reducing the pressure in said first cuff means at a predetermined rate;
means for filtering out blood pulses from the monitored pressure in the second cuff means to obtain a filtered pressure;
means for monitoring the time rate of change of the filtered pressure in said second cuff means, and for determining when said filtered pressure in said second cuff means passes through a plurality of relative minimum values and when said filtered pressure in said second cuff means exhibits inflection points; and
means for associating values of pressure in said first cuff means at the time at which the filtered pressure in said second cuff means passes through a smallest of said relative minimum values and said inflection points with the systolic and mean arterial blood pressures of the patient, respectively.

8. The apparatus of claim 7 comprising:
a means for determining inflection points in the filtered pressure after systolic pressure has occurred;
a means for determining a second derivative of the filtered pressure and magnitudes of the second derivative corresponding to the inflection points;
a means for relating a most negative of these magnitudes of the second derivative with a corresponding occlusion bladder pressure to derive mean arterial pressure.

9. The system of claim 8, comprising:
a means for deriving first, second, and third derivatives of the static pressure signal;
a means for recognizing positive-going, zero-crosses of the first derivative;
a means for storing a static pressure value corresponding to each zero-cross of the first derivative, each static pressure value comprising a relative minimum of the static pressure signal, the smallest of which corresponds to systolic pressure.

10. The system of claim 9, comprising;
a means for determining positive-going, zero-crosses of the third derivative;
a means for storing negative values of the second derivative corresponding to the zero-crosses of the third derivative; and
a means for relating a most negative value of the stored negative values of the second derivative to a corresponding occlusion bladder pressure to derive mean arterial pressure.

11. The system of claim 10, comprising;
a means for determining if two or more stored negative values are equal, for determining occlusion bladder pressures corresponding to the two or more equal stored negative values, and for averaging these occlusion bladder pressures to derive mean arterial pressure.

12. The system of claim 11, comprising;
a means for defining a region of the static pressure signal within which mean arterial pressure occurs, the region beginning with a first static pressure value corresponding to systolic pressure and ending with a maximum static pressure value occurring after the first static pressure value.

* * * * *